(12) United States Patent
Romanelli et al.

(10) Patent No.: US 9,831,709 B2
(45) Date of Patent: Nov. 28, 2017

(54) METHOD AND APPARATUS FOR WIRELESS CHARGING OF A BIOELECTRONIC DEVICE IMPLANTED IN A LABORATORY ANIMAL OR IN A HUMAN BEING

(71) Applicant: AB Medica S.p.A., Milan MI (IT)

(72) Inventors: Pantaleo Romanelli, Milan MI (IT); Antonino Paris, Milan MI (IT); Stefano Marchetti, Milan MI (IT)

(73) Assignee: AB MEDICA HOLDING S.P.A., Milan (MI) (IT)

( * ) Notice: Subject to any disclaimer, the term of this patent is extended or adjusted under 35 U.S.C. 154(b) by 439 days.

(21) Appl. No.: 14/406,783

(22) PCT Filed: Jun. 18, 2013

(86) PCT No.: PCT/IB2013/055009
§ 371 (c)(1),
(2) Date: Dec. 10, 2014

(87) PCT Pub. No.: WO2013/190471
PCT Pub. Date: Dec. 27, 2013

(65) Prior Publication Data
US 2015/0180267 A1  Jun. 25, 2015

(30) Foreign Application Priority Data
Jun. 18, 2012  (IT) .............................. MI2012A1049

(51) Int. Cl.
*H02J 7/00* (2006.01)
*H02J 7/02* (2016.01)
(Continued)

(52) U.S. Cl.
CPC .............. *H02J 7/025* (2013.01); *A01K 1/031* (2013.01); *A01K 11/006* (2013.01);
(Continued)

(58) Field of Classification Search
CPC ........ H02J 7/025; H02J 7/0042; H02J 7/0052; H02J 7/04; H02J 17/00; H02J 5/005;
(Continued)

(56) References Cited

U.S. PATENT DOCUMENTS

| 5,258,766 A | 11/1993 | Murdoch |
| 2003/0150395 A1 | 8/2003 | Mauderli et al. |

(Continued)

FOREIGN PATENT DOCUMENTS

| CN | 1168625 A | 12/1997 |
| CN | 101234021 A | 8/2008 |

(Continued)

OTHER PUBLICATIONS

International Search Report issued in PCT Application No. PCT/IB2013/055009.

(Continued)

*Primary Examiner* — Nha Nguyen
(74) *Attorney, Agent, or Firm* — Lucas & Mercanti, LLP

(57) ABSTRACT

The invention relates to an apparatus for charging a remote feedable circuit bioelectronic implanted in a patient or in a laboratory animal, said apparatus comprising a composable container configured to define a closed environment suitable to receive a patient or a laboratory animal, said container comprising a plurality of composable walls made of a nonmagnetic material and connected to each other so as to define said closed environment, said container comprising at least one first winding whose axis is arranged in a first direction (Z) and at least one second winding whose axis is arranged in a second direction (Y) perpendicular to said first direction (Z). The apparatus further comprises a system for powering and driving the windings of the composable container, said system comprising a switching power driver for each winding, a plurality of phase locked loop circuits
(Continued)

respectively connected to each switching power driver and connected to a programmable logic circuit of the powering and driving system, said programmable logic circuit being configured to perform a phase comparison, the programmable logic circuit being in turn connected to a microprocessor of the powering and driving system, said microprocessor being configured to provide driving signals to the windings for generating inside the container a rotating magnetic field.

10 Claims, 3 Drawing Sheets

(51) Int. Cl.
*A01K 1/03* (2006.01)
*A01K 11/00* (2006.01)
*A61B 5/00* (2006.01)
*H01F 38/14* (2006.01)
*H02J 7/04* (2006.01)
*H02J 5/00* (2016.01)
*H02J 17/00* (2006.01)

(52) U.S. Cl.
CPC .......... *A61B 5/6846* (2013.01); *H01F 38/14* (2013.01); *H02J 7/0042* (2013.01); *H02J 7/0052* (2013.01); *H02J 7/04* (2013.01); *A61B 2503/40* (2013.01); *A61B 2560/0219* (2013.01); *H02J 5/005* (2013.01); *H02J 17/00* (2013.01)

(58) Field of Classification Search
CPC ....... H01F 38/14; A01K 1/031; A01K 11/006; A61B 5/6846; A61B 2560/0219; A61B 2503/40
See application file for complete search history.

(56) References Cited

U.S. PATENT DOCUMENTS

| | | | |
|---|---|---|---|
| 2004/0111840 A1 | 6/2004 | Gyongyosi et al. | |
| 2004/0211840 A1 | 10/2004 | Yogev et al. | |
| 2007/0296393 A1* | 12/2007 | Malpas | A61B 5/0002 323/355 |
| 2010/0181962 A1 | 7/2010 | Chen et al. | |

FOREIGN PATENT DOCUMENTS

| | | |
|---|---|---|
| CN | 102013717 A | 4/2011 |
| JP | S61136609 U | 8/1986 |
| JP | H03502269 A | 5/1991 |
| JP | 2001148608 A | 5/2001 |
| JP | 2003157907 A | 5/2003 |
| JP | 2003260026 A | 9/2003 |
| JP | 2004159456 A | 6/2004 |
| JP | 2008283791 A | 11/2008 |
| JP | 2010119456 A | 6/2010 |
| WO | 8905530 A1 | 6/1989 |
| WO | 2010144494 | 12/2010 |
| WO | 2012143850 | 10/2012 |

OTHER PUBLICATIONS

Chinese Office Action for Corresponding Chinese Application No. 201380032377.9 (dated Sep. 30, 2015) (17 Pages).
Japanese Office Action for Corresponding Japanese Application No. 2015-517902 (dated Jan. 23, 2017) (5 Pages).
Chinese Office Action for Corresponding Chinese Application No. 201380032377.9 (dated Jun. 3, 2016) (7 Pages).

* cited by examiner

METHOD AND APPARATUS FOR WIRELESS CHARGING OF A BIOELECTRONIC DEVICE IMPLANTED IN A LABORATORY ANIMAL OR IN A HUMAN BEING

CROSS-REFERENCE TO RELATED APPLICATIONS

This application is a 371 of PCT/IB2013/055009, filed Jun. 18, 2013, which claims the benefit of Italian Patent Application No. MI2012A001049, filed Jun. 18, 2012, the contents of each of which are incorporated herein by reference.

FIELD OF THE INVENTION

The present invention relates to an apparatus and a method of wireless charging in a resonant mode of bioelectronic devices implanted in laboratory animals or human beings.

BACKGROUND OF THE INVENTION

It is known that scientific experiments on laboratory animals are an essential step towards the clinical use of biomedical devices, especially bioelectronic devices, and that the installation of experimental bioelectronic devices in laboratory animals is constantly growing.

There are also already known experimental protocols, e.g. in the treatment of epilepsy, based on the implant of systems for the acquisition and monitoring of brain bioelectric signals in human beings.

Charging of these bioelectronic devices may be performed by using appropriate cables or in a wireless mode by electromagnetic induction. The latter mode is preferred because the use of cables is a source of infection for laboratory animals as well as for patients, which cannot be eliminated but removing the implanted device, thus resulting in the interruption of experimental activities or therapies. The elimination of supply cables, which are external bodies having a not negligible size, also prevents laboratory animals and patients from experiencing behavioral problems during the experimental activity or therapy.

In order to perform wireless charging it is necessary to magnetically couple a winding of a power supply device, such as an inductive coupler, with a corresponding winding of a power supply circuit associated with the implanted bioelectronic device. To this aim the two windings must be aligned, which requires to hold the laboratory animal or the patient still for the whole time of the experimental activity and/or the complete charging of a rechargeable battery of the bioelectronic implanted device. This situation can be easily managed in the case of a human being thanks to the cooperation of the patient, but in the case of a laboratory animal it is necessary to resort to holding means or even to anesthesia, with serious ethical and organizational problems.

In the specific case of laboratory animals, confinement cages have been developed that are provided with a plurality of windings arranged below the floor on which a laboratory animal can move. The windings can generate a plurality of magnetic fields which are mutually parallel and directed along a vertical axis, whereby the laboratory animal housed in the cage may freely move between the parallel magnetic fields and the power supply circuit of the implanted bioelectronic device is substantially always coupled with at least one of them, so that it may be powered independently of the position of the laboratory animal within the cage.

There are also known power supply systems associated with cages for laboratory animals in which a cage is fully inserted in a winding capable of generating a magnetic field, for example parallel to its axis.

These solutions are very effective in the case of four-legged laboratory animals, such as mice, in which bioelectronic devices can be implanted in a position substantially parallel to the floor, e.g. in the abdomen, but they have proved totally unsuitable for the power supplying bioelectronic to devices implanted in laboratory animals such as monkeys, which have a much greater mobility and continuously move with great agility in the whole available space, e.g. by climbing on the grates forming walls and ceiling of a cage.

A similar but more serious problem arises with patients with implanted bioelectronic devices remotely supplied such as the device disclosed in the patent publication WO 2012/143850 A1 in the applicant's name. A patient in fact cannot be confined in a cage and must be accommodated on a bed or chair for the time necessary to recharge the batteries of the implanted device, which is generally carried out by way of power supply devices comprising windings placed directly in contact with the patient's body in the area where the bioelectronic device is implanted. This condition is poorly tolerated by patients because it requires them to remain substantially still for a relatively long time.

SUMMARY OF THE INVENTION

Therefore a charging apparatus would be desirable suitable to charge batteries of a bioelectronic device in a wireless mode without restricting the movements of a patient or laboratory animal wherein the bioelectronic device is installed, which is an object of the present invention. Said object is achieved with an apparatus and a method of charging as defined in the appended claims.

An idea of solution underlying the present invention is to use the wireless power supply technology in a resonant mode, which is generally employed for devices that require large amounts of energy, such as e.g. electrical machines, robots, vacuum cleaners or laptop computers. According to the wireless power supply mode there are used a first winding connected to a power supply as a transmitting unit and a second winding connected to the device to be powered as a receiving unit, wherein both windings are configured to have the same resonance frequency. By exploiting this principle, the apparatus according to the invention comprises a composable container in turn comprising one or more compartments every one of which is associated with at least one first winding, whose axis is arranged in a first direction, and at least one second winding, whose axis is arranged in a second direction perpendicular to the first direction. The composable container also includes a system for powering and driving the windings configured to create inside it a rotating magnetic field in a plane defined by the axes of the windings.

Thanks to these characteristics it is possible to maintain the power supply circuit of a bioelectronic implanted device magnetically coupled to the rotating magnetic field in the container without forcing the patient or the laboratory animal to immobility.

The composable container may be configured either as a cage for laboratory animals or as an environment suitable to accommodate a human being, that may e.g. be integrated in a hospital room or in the room of a house.

According to an embodiment of the invention, the composable container may comprise for each compartment at least one third winding, whose axis is arranged in a third direction perpendicular to the first and second directions. This configuration allows to drive the three windings so as to obtain a rotation of the magnetic field no longer on a plane but in the space, i.e. with respect to all the planes defined by the axes of the three windings.

According to a preferred embodiment of the invention a first pair of identical windings arranged coaxially to each other and mutually spaced in the first direction are associated to each compartment of the composable container and supplied so as to generate magnetic fields along the same direction, as well as a second pair of identical windings arranged coaxially to each other and mutually spaced in the second direction, that are supplied so as to generate magnetic fields along the same direction. The windings of each pair are e.g. dimensioned and arranged as Helmholtz windings, allowing to generate a magnetic field between them that is substantially uniform in the direction of their axes. In the case of cages for laboratory animals, whose size meets the present field standards, the windings are dimensioned and arranged so as to be as close as possible to this ideal condition.

This configuration is particularly useful in large environments and is therefore preferred for the application of the invention to cages for laboratory animals characterized by high mobility, e.g. primates, and to environments suitable to accommodate human beings, such as hospital or house rooms. A single winding for each direction may in fact lead to a weak magnetic field at the opposite end of the container in that direction, which is unsuitable for a bioelectronic device implanted in a human being or in a laboratory animal confined in the container. The use of pairs of windings, preferably arranged at opposite faces of the composable container, allows instead to maintain substantially the same value of the magnetic field from side to side and/or from the floor to the ceiling of the container, thus allowing powering of the bioelectronic device anywhere inside the container even when the patient or the laboratory animal are moving.

The composable container according to the invention may advantageously comprise for each compartment a third pair of windings which, similarly to those of the first and of the second pair, are identical to each other and arranged coaxially, mutually spaced in the third direction of the container, perpendicular to the first and second direction, and supplied so as to generate magnetic fields in the same direction. This configuration allows to drive the three pairs of windings so as to obtain a rotation of the magnetic field in the space, i.e. relative to all the planes defined by the axes of the three windings.

The windings of each pair are preferably arranged outside the composable container at its opposite faces, or integrated inside the panels that form its structure. This advantageously allows to maximize the internal space available and to avoid accidental contact of a patient or a laboratory animal with the windings, wherein current circulates.

According to a further aspect of the invention, at least one sensor suitable to detect the presence of a patient or a laboratory animal may be advantageously mounted in each compartment of the container, thus making it possible to activate only the windings associated with the compartment that is occupied and hence to optimize their operation and energy consumption by avoiding to supply windings of empty compartments.

The claims as filed are a part of this description, and are incorporated herein by express reference.

BRIEF DESCRIPTION OF THE DRAWINGS

Further advantages and features of the present invention will become clear to those skilled in the art from the following detailed and non-limiting description of embodiments thereof with reference to the attached drawings in which.

Figure 1A:
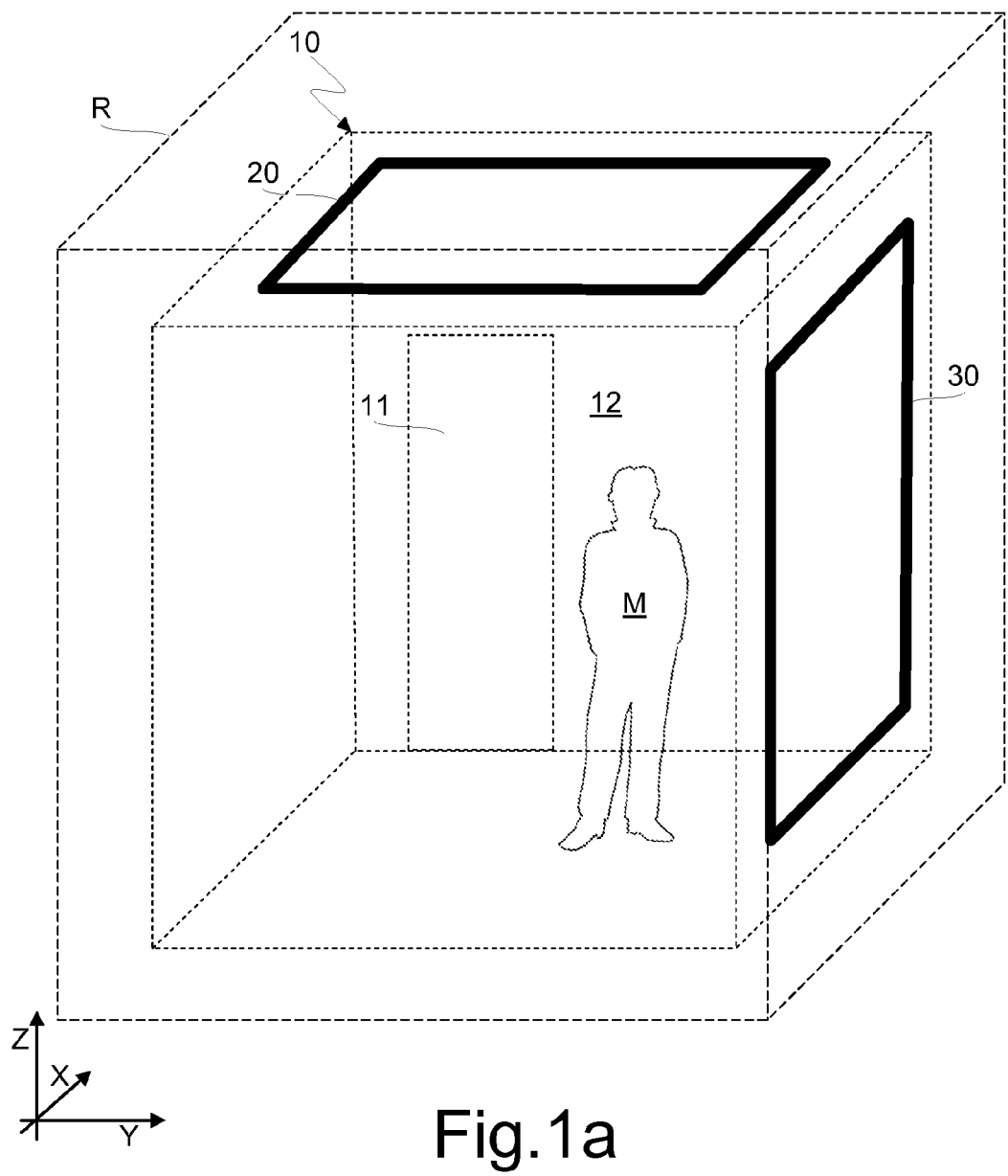
FIG. 1a is a perspective view showing a composable container according to a first embodiment of the present invention installed in a room suitable to accommodate a human being.

The charging apparatus according to the present disclosure includes a composable container, indicated with reference numeral 10, that is provided with at least two windings 20, 30 arranged with mutually perpendicular axes, and with a system for powering and driving the windings that will be described in detail below.

Figure 1B:
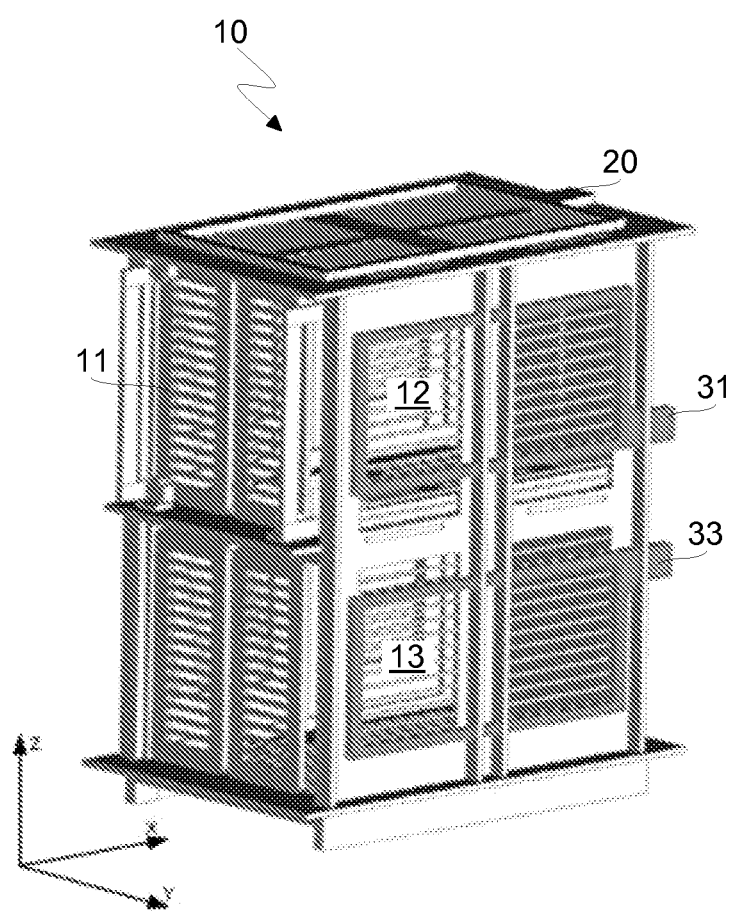
FIG. 1b is a perspective view showing a composable container configured as a cage for laboratory animals according to an alternative embodiment of the present invention.

As schematically shown in FIG. 1a, the composable container can be configured as a living environment and be installed in a room R, such as a hospital or a house room, for charging a wireless rechargeable bioelectronic circuit implanted in a human being M, or be configured as a cage for laboratory animals, schematically shown in FIG. 1b, for charging a wireless rechargeable bioelectronic circuit implanted in a laboratory animal.

DETAILED DESCRIPTION OF THE INVENTION

In both cases the composable container comprises a plurality of composable walls forming a closed environment. The only differences between the room of FIG. 1a and the cage of FIG. 1b concern their size and possibly their shape. Furthermore, in case of installation in a room, in particular in a house, the composable container 10 may be suitably provided with aesthetic elements, for example panels, configured to allow a complete integration thereof in the room so as not to be visible to a patient.

In order to understand operation of the apparatus of the invention it is substantially irrelevant whether the composable container 10 is integrated in a room R rather than used as a cage for laboratory animals. For this reason, the invention will be illustrated with exclusive reference to the case of a cage for recharging bioelectronic circuits implanted in laboratory animals, being it clear that what will be said for the cage is also valid, mutatis mutandis, also when the composable container is installed in a room for patients.

Referring to FIG. 1b, the composable container or cage 10 according to the invention comprises a plurality of modular panels made of a nonmagnetic material. The cage 10 is provided with at least one door 11 and defines at least one inner compartment 12 suitable to accommodate a laboratory animal. Due to reasons of hygiene and costs, the nonmagnetic material is preferably a plastic material, for example PA6.

In the illustrated embodiment, the cage 10 comprises in particular two intercommunicating compartments 12, 13 which are arranged on top of each other in a first direction Z that goes from the base to the ceiling of the cage 10.

The cage 10 according to the invention is configured so as to allow wireless power supply in a resonant mode of a generic bioelectronic device implanted in a laboratory animal housed therein, possibly provided with a rechargeable battery, such as an implantable device for the acquisition and monitoring of bioelectric signals from the brain, as well as for intracranial stimulation.

To this end the cage 10 comprises in each compartment at least one first winding 20 whose axis is e.g. arranged in the first direction Z and at least one second winding 30, whose the axis is arranged in a second direction Y of the cage, perpendicular to the first direction Z, for example a transverse direction Y.

The windings 20, 30 are arranged so as to be not accessible to the laboratory animal confined in the cage 10 and for this purpose they may be mounted at the outside thereof or in respective cavities formed in the walls. The electrical terminals of the windings 20, 30 are similarly arranged so as to be accessible from outside the container 10 when it is assembled, so that they can be easily connected while avoiding that the laboratory animal may interfere.

The cage 10 also comprises a system for powering and driving the windings 20, 30 configured to generate magnetic fields in the first and in the second directions Z, Y, and provide control signals suitable to create inside the cage 10 a rotating magnetic field on a plane defined by the axes of the windings.

According to a preferred embodiment of the invention, the composable container 10 comprises a first pair of identical windings arranged coaxially to each other and mutually spaced in the first direction Z. The container also comprises a second pair of identical windings arranged coaxially to each other and mutually spaced in the second direction Y. The windings of each pair are supplied so as to generate magnetic fields along the same direction.

Figure 2:
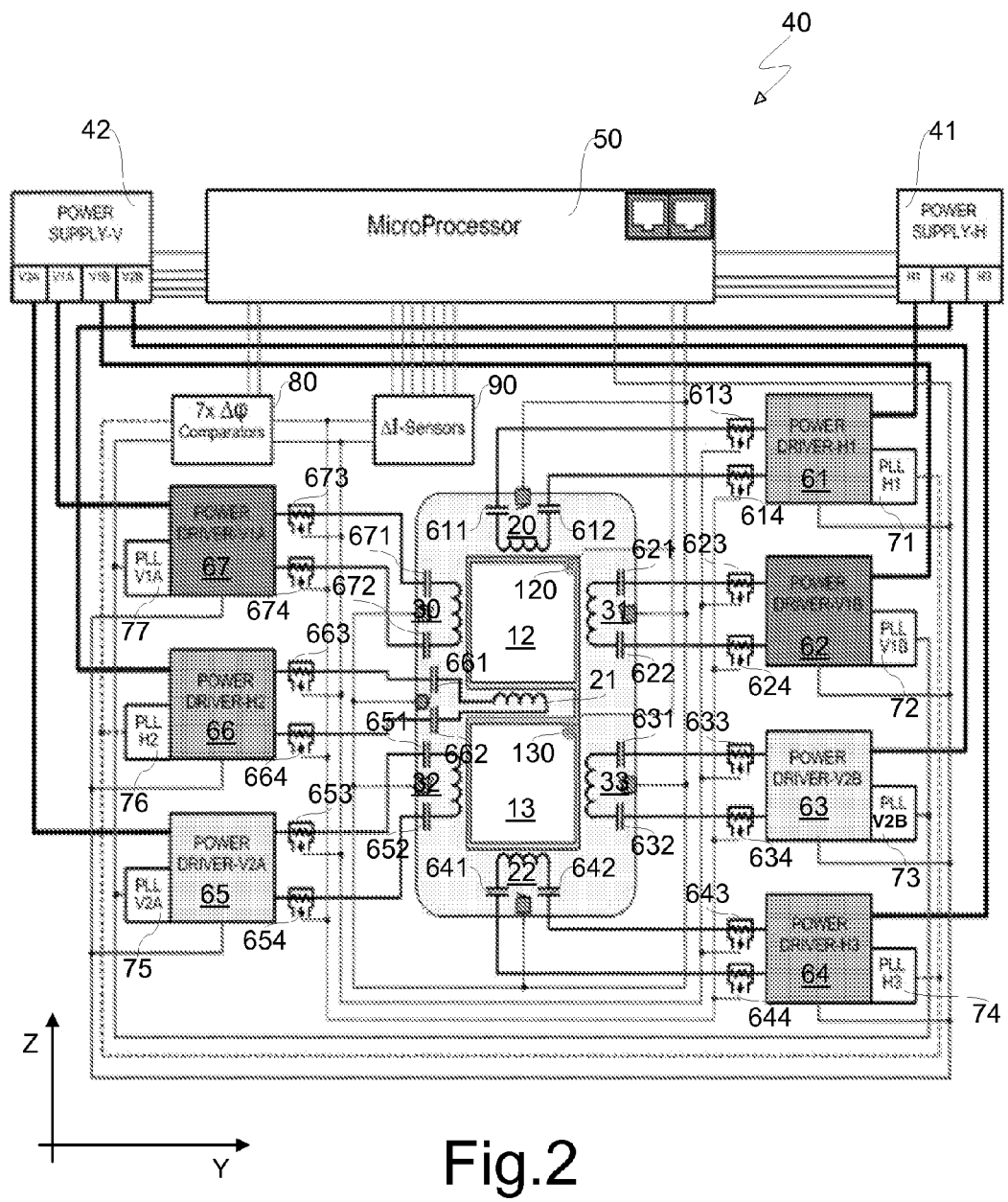
FIG. 2 shows a block diagram of a system for powering and driving the windings associated with the composable container of FIG. 1b.

In the embodiment of the charging apparatus shown in FIGS. 1b and 2, the cage 10 comprises for each compartment 12, 13 a pair of first identical windings arranged coaxially to each other in the first direction Z of the cage 10 and mutually spaced in such direction. The cage 10 also comprises for each compartment a pair of second identical windings arranged coaxially to each other in the second direction Y of the cage 10 and mutually spaced in this direction.

The windings of each pair are configured and arranged so as to constitute the Helmholtz coils, capable of generating a substantially uniform magnetic field in the direction of their axes, which is directly proportional to the number of turns and to the current that circulates therethrough.

The windings associated with each compartment 12, 13 of the cage 10 are respectively indicated by reference numerals 20, 21, 22 in the first direction Z and by reference numerals 30, 31 and 32, 33 in the second direction Y. In the perspective view of FIG. 1b only the windings 20, 31 and 33 are visible.

It will be understood that the arrangement of the two compartments 12, 13 one above the other in the first direction Z allows to use only three instead of four windings to generate the magnetic field in this direction, because the intermediate winding 21 can form a pair either with winding 20 or with winding 22.

The windings 20, 21, 22 and 30, 31, 32, 33 are associated with resonant circuits that are configured so as to have a resonance frequency equal to that of the winding of the resonant circuit powering the bioelectronic device implanted in the laboratory animal, thus enabling its operation as well as charging of its rechargeable battery, if any.

The powering and driving system, generally designated by reference numeral 40, comprises at least one AC/DC power supply connected in parallel to the windings and having adjustable voltage outputs.

In the embodiment shown in FIG. 2, the powering and driving system 40 comprises in particular a first power supply 41 coupled to the first windings 20, 21, 22 that have axes oriented in the first direction Z and a second power supply 42 coupled to the second windings 30, 31, 32, 33 that have axes oriented in the second direction Y.

The powering and driving system 40 also comprises a microprocessor 50 provided with a suitable management software and feedback control of the windings.

The powering and driving system 40 comprises a "switching power driver" for each winding, which is supplied by the respective AC/DC. In the embodiment shown in FIG. 2, the switching power drivers are respectively indicated by reference numerals 61 to 67 and are configured to generate driving signals at a predetermined frequency.

The driving signals are preferably voltage signals, such as e.g. square wave signals, and have values of frequency corresponding to the resonance frequency of the resonant circuit. These driving signals preferably have voltage values lower than or equal to 60 V.

As it is well known to a person skilled in the art, in order to determine the resonant frequency of a resonant circuit, parasitic capacitance in parallel of the windings must be taken into account, the windings being characterized by their so-called "self-resonance frequencies", namely frequencies determined by the inductance of each winding and the respective parasitic capacitance in parallel, above which the windings behave as a capacity and not as an inductance. In order to be reasonably sure that the windings behave as inductances at the desired frequency and that the parasitic capacitances substantially have no effect, the windings are preferably dimensioned so as to have self-resonance frequencies at least ten times higher than the resonance frequency desired for the resonant circuit. At the ends of each winding two capacitors arranged in series are connected, forming with the winding a balanced resonant serial circuit suitable to maximize the merit factor at the driving frequency. In the illustrated embodiment, the capacitors are respectively indicated by reference numerals 611, 612, 621, 622, 631, 632, 641, 642, 651, 652, 661, 662, 671, 672, so that the cage 10 comprises seven resonant circuits operating in parallel.

For each resonant circuit, the values of the capacitance of the capacitors and the inductance of the respective winding are dimensioned so as to obtain a resonance frequency equal to that of the driving signal generated by the power driver connected thereto.

A phase locked loop circuit or PLL is connected to each power driver. PLL circuits are all connected to a programmable logic circuit 80 configured to compare signal phases, the programmable logic circuit being connected to the microprocessor 50. In the illustrated embodiment, PLL circuits are indicated with reference numerals 71 to 77.

During operation of the powering and driving system 40, each power driver 61, . . . , 67 generates a driving signal that causes a current to circulate through the resonant circuit connected thereto. Power supply is managed to generate magnetic fields having the same direction in the windings of each pair of windings.

The control signals of the power drivers 61, . . . , 67 are synchronized with each other on the basis of a reference signal that is preferably a pilot signal generated by one of the power drivers connected to the resonant circuits of the cage 10, for example the resonant circuit of winding 21. Starting from the phase of this pilot signal all the other resonant circuits present on the cage 10 are synchronized in the same direction through the relative PLL circuit 71, . . . , 77.

PLL circuits 71, ..., 77 particularly allow to detect phase shift values between the currents actually circulating in the windings and their frequency, and to adjust the control signals of the power driver through the programmable logic circuit 80 for the phase comparison connected to the microprocessor 50, in order to compensate for differences between the actual values of mutual current phase shifts compared to the corresponding nominal values. The frequency of the currents is tuned to a desired frequency, in particular to a frequency allowing to transfer the maximum possible power to the windings, which can be determined for example with an algorithm of the type "maximum power point tracking", well known to one skilled in the art.

The differences between actual values of phase shifts are in fact subject to fluctuations mainly due to the movement of the laboratory animal or the patient inside the container 10, as well as to the presence of other people in the container 10 together with the patient, and also to variations of the operation temperature of the apparatus 1, manufacturing tolerances of the electronic components, external e.g. electromagnetic disturbances and the like, that may alter the resonance frequency. Tuning of the resonance frequency is therefore important to achieve the maximum possible power transfer and to optimize operation of the apparatus.

The reference signal is distributed from the programmable logic circuit 80, which is adapted to perform a phase comparison between the control signals through a data bus.

Once synchronization of the windings of the resonant circuits in the first direction Z has been carried out, the circuit 80 in programmable logic generates a second synchronization signal that is delayed phase-shifted, for example by 90°, with respect to the synchronism reference signal. The windings having axes arranged in the perpendicular direction, for example in the second direction Y are driven by this phase-shifted driving signal.

Therefore, the windings arranged with the axes in the second direction Y are synchronized with each other, but driven by a phase-shifted signal with respect to the windings arranged in the first direction Z.

It will be understood that, by virtue of this driving mode based on phase-shifted signals and by virtue of the spatial arrangement of the windings on mutually perpendicular planes, the magnetic field present inside the cage is a vector rotating in the YZ plane. This allows the winding of the resonant circuit of the bioelectronic device implanted in the laboratory animal to be coupled with the magnetic field present in the cage regardless of its position relative to the YZ plane, thus allowing operation of the bioelectronic device and/or recharging of its battery regardless of the position of the laboratory animal inside the cage 10. In other words, the laboratory animal housed in the cage 10 is free to move during operation of the bioelectronic device and/or charging of its battery in any zone of the cage 10 and also from one floor to another thereof, favoring execution of scientific and experimental activities.

The magnetic coupling is maximum when the winding of the resonant circuit of the bioelectronic device implanted in the laboratory animal is located in a plane perpendicular to the YZ plane, thus allowing to maximize energy transfer. Otherwise there will be a poorer coupling with a lower energy transfer, or no magnetic coupling nor energy transfer at all when the resonant circuit powering the bioelectronic implanted device is parallel to the YZ plane.

It will be understood that this driving mode is not limited to the preferred embodiment of the invention, which comprises a pair of parallel coaxial windings in the first and second directions Y, Z, respectively for each compartment of the cage 10, but is also equally applicable when the composable container comprises only a first and a second winding with mutually perpendicular axes, the only difference being that the presence of a single winding in any direction does not result in the generation of magnetic fields having the same direction along the first and the second directions.

According to a further embodiment of the invention, in order to obtain a rotation of the magnetic field vector in the space rather than on a plane it is possible to associate to each compartment of the compartment 10 at least one third winding arranged in a third direction of the cage 10, for example a longitudinal direction X perpendicular to the transverse and vertical directions Y and Z, for example a third pair of windings (not shown) identical to each other and arranged coaxially and mutually spaced in the third direction X of the cage 10.

Due to the configuration with three windings, or pairs of windings, arranged on planes perpendicular to each other, the magnetic field vector has a spatial orientation. By suitably shifting the driving signals of the three windings, or pairs of windings, for example by 90°, a rotation of the magnetic field vector in the space is obtained allowing power supply of the bioelectronic implanted device regardless of the position of the laboratory animal not only with respect to the YZ plane, but also with respect to XY and XZ planes.

Each resonant circuit of the powering and driving system 40 further comprises a pair of current sensors with transformer arranged along the cables that connect the power driver to the capacitors arranged at the ends of the winding and adapted to measure the current supplied to the capacitors and the windings. In the embodiment shown in FIG. 2, the current sensors with transformer are respectively indicated by reference numerals 613, 614, 623, 624, 633, 634, 643, 644, 653, 654, 663, 664, 673, 674. The current values measured by the current sensors are sent to a block 90 of the powering and driving system 40, which is connected to the microprocessor 50. The block 90 performs a difference between the current values to check for any current leakage to ground. In the case of leakages e.g. due to poor insulation or accidental contact with an operator, the microprocessor 50 interrupts operation of the power driver associated with the leakage.

From a manufacturing point of view, the capacitors associated to each winding are preferably accommodated in a container housed in a frame that houses the winding. In the same container in addition to the capacitors there are also an opening sensor, for example a micro switch, and an identification system of the winding, for example a resistor, which report their status and value to a microprocessor of the powering and driving system 40 through a data bus. The opening sensor interrupts operation of the power driver of the respective winding if the container of the capacitors is accidentally opened. The identification system of the winding is used to determine whether during wiring the association between the power driver and the respective winding is performed correctly.

According to a further aspect of the invention, the powering and driving system 40 further comprises at least one sensor suitable to detect the presence of a human being or a laboratory animal inside the container 10. With reference to the embodiment shown in FIG. 1*b*, for example, the container comprises one detection sensor for each compartment 12, 13, for example an infrared type sensor. Correspondingly, in the block diagram of FIG. 2 two sensors of infrared type 120, 130 are schematically shown, which are respectively inserted into each compartment 12, 13.

In a configuration of the cage 10, and more generally of the composable container, having intercommunicating compartments, the provision of at least one detection sensor for each compartment allows to generate the magnetic field only in the compartment where the laboratory animal is actually present, which offers the possibility to optimize the operation of the cage 10 from the point of view of energy consumption.

The embodiments of the invention herein described and illustrated are only examples susceptible of numerous variants. For example, it is possible to remotely control operation of the container 10 through suitable appropriate Ethernet ports provided in the microprocessor 50 block. Moreover, the powering and driving system 40 may be housed in a special container connected to the windings and mountable on a wall of a room intended for housing the container 10 or directly on the container, thereby facilitating its displacement and installation.

The invention claimed is:

1. An apparatus for charging a remote feedable circuit bioelectronic implanted in a patient or in a laboratory animal, said apparatus comprising:
  a) a composable container configured to define a closed environment suitable to receive a patient or a laboratory animal, said container comprising a plurality of composable walls made of a nonmagnetic material and connected to each other so as to define said closed environment, said container comprising at least one first winding whose axis is arranged in a first direction (Z) and at least one second winding whose axis is arranged in a second direction (Y) perpendicular to said first direction (Z), said windings being installed in or on the walls and configured so as to:
    be not accessible to the patient and/or laboratory animal confined in the container,
    have electrical terminals accessible only from the outside of the container when it is mounted,
    radiate an electromagnetic field, when supplied with alternating current, towards the inside of said closed environment along said first direction (Z) and said second direction (Y); and
  b) a system for powering and driving the windings of the composable container, comprising:
    a switching power driver for each winding,
    a plurality of phase locked loop circuits respectively connected to each switching power driver and to a programmable logic circuit of the powering and driving system, said programmable logic circuit being configured to perform a phase comparison, the programmable logic circuit being in turn connected to a microprocessor of the powering and driving system, said microprocessor being configured to provide driving signals to the windings for generating inside the container a rotating magnetic field.

2. The charging apparatus according to claim 1, wherein at least one capacitor is connected at the terminals of each winding forming therewith a resonant circuit connected to a respective switching power driver, and wherein the values of the capacitance of the capacitors and of the inductance of the windings of each resonant circuit are dimensioned so that the resonant circuit resonates at a frequency corresponding to the frequency of a driving signal generated by the respective switching power driver.

3. The charging apparatus according to claim 1, comprising a pair of first identical windings arranged coaxially to each other and mutually spaced in said first direction (Z) of the container, as well as a pair of second identical windings arranged coaxially to each other and mutually spaced in the second direction (Y) of the container, perpendicular to the first direction (Z), wherein the windings of each pair are configured and arranged so as to form Helmholtz coils and said powering and driving system of the windings is configured to power the windings of each pair so as to generate magnetic fields having the same direction and to provide control signals suitable to generate inside the container a rotating magnetic field in a plane identified by the first and second directions (Z, Y).

4. The charging apparatus according to claim 1, further comprising at least one third winding whose axis is arranged in a third direction (X) of the container, perpendicular to the first and second directions (Z, Y).

5. The charging apparatus according to claim 4, comprising a pair of identical third windings arranged coaxially to each other and mutually spaced in said third direction (X), and wherein the windings of each pair are configured and arranged so as to form Helmholtz coils and said powering and driving system of the windings is configured to power the windings of each pair so as to generate magnetic fields having the same direction and to provide control signals suitable to generate inside the compartment a rotating magnetic field in the space.

6. The charging apparatus according to claim 2, wherein each resonant circuit of the powering and driving system further comprises a pair of current sensors with transformer arranged along the cables that connect the respective switching power driver to the capacitors arranged at the ends of the winding and adapted to measure the current supplying the capacitors and the windings, the powering and driving system also comprising a block connected to the microprocessor and configured to perform differences between current values in order to check for any current leakage to ground.

7. The charging apparatus according to claim 1, wherein the powering and driving system further comprises at least one sensor suitable to detect the presence of a human being or a laboratory animal in each compartment of the container.

8. The charging apparatus according to claim 1, wherein said composable container is configured as a living environment.

9. The charging apparatus according to claim 1, wherein said composable container is configured as a cage for laboratory animals.

10. A method for the wireless charging in resonant mode of a bioelectronic device implanted in a laboratory animal or in a patient, said method comprising the following steps:
  i) providing and installing an apparatus according to claim 1;
  ii) confining a laboratory animal or a patient in the composable container of said apparatus;
  iii) generating control signals in order to supply the windings of the container with respective alternating currents having nominal reference amplitudes and phase shifts suitable to generate a rotating magnetic field inside the container;
  iv) generating detection signals of the currents actually circulating in said windings;
  v) evaluating through said detection signals actual values of mutual phase shift and frequency of the currents actually circulating in the windings;
  vi) adjusting the driving signals in order to compensate for differences between the actual the phase shifts and the corresponding nominal values; and vii) tuning the frequency of said currents to a desired frequency so as to maximize power transfer to the windings.

\* \* \* \* \*